(12) United States Patent
Yoon et al.

(10) Patent No.: US 10,357,228 B2
(45) Date of Patent: Jul. 23, 2019

(54) IMAGE PROCESSING METHOD AND APPARATUS

(71) Applicant: SAMSUNG ELECTRONICS CO., LTD., Suwon-si (KR)

(72) Inventors: Hee-chul Yoon, Seoul (KR); Hyun-taek Lee, Seoul (KR); Hae-kyung Jung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 610 days.

(21) Appl. No.: 13/855,338

(22) Filed: Apr. 2, 2013

(65) Prior Publication Data

US 2013/0281862 A1 Oct. 24, 2013

Related U.S. Application Data

(60) Provisional application No. 61/635,425, filed on Apr. 19, 2012.

(30) Foreign Application Priority Data

Oct. 23, 2012 (KR) .................. 10-2012-0117913

(51) Int. Cl.
*A61B 8/00* (2006.01)
*A61B 8/08* (2006.01)
*A61B 8/06* (2006.01)

(52) U.S. Cl.
CPC ............ *A61B 8/5223* (2013.01); *A61B 8/065* (2013.01); *A61B 8/0883* (2013.01); *A61B 8/488* (2013.01); *A61B 8/52* (2013.01)

(58) Field of Classification Search
None
See application file for complete search history.

(56) References Cited

U.S. PATENT DOCUMENTS

| 5,415,171 A | 5/1995 | Goh et al. |
| 6,792,308 B2 | 9/2004 | Corbucci |

(Continued)

FOREIGN PATENT DOCUMENTS

| CN | 1868407 A | 11/2006 |
| CN | 101523435 A | 9/2009 |

(Continued)

OTHER PUBLICATIONS

Karatzis et al., "Myocardial Performance Index (Tei Index): Evaluating its Application to Myocardial Infarction", Hellenic Journal of Cardiology, 2009, pp. 60-65.*

(Continued)

*Primary Examiner* — Christopher L Cook
(74) *Attorney, Agent, or Firm* — Sughrue Mion, PLLC

(57) ABSTRACT

An image processing method and an image processing apparatus are provided. The image processing method measures a myocardial performance index (MPI), the image processing method including: obtaining a region of interest (ROI) for measuring the MPI, based on signal levels of an input signal and an output signal of a heart spectrum image; obtaining a plurality of marker areas, within the obtained ROI, wherein at least one marker for measuring the MPI is located in each of the plurality of marker areas, based on at least one from among a feature value of the input signal and a feature value of the output signal; and obtaining the at least one marker for each of the plurality of marker areas.

28 Claims, 9 Drawing Sheets

(56) References Cited

U.S. PATENT DOCUMENTS

| | | | |
|---|---|---|---|
| 7,192,399 | B2 | 3/2007 | Kjellstrom et al. |
| 7,689,283 | B1 | 3/2010 | Schecter |
| 8,204,288 | B2 | 6/2012 | Kim et al. |
| 2002/0151938 | A1 | 10/2002 | Corbucci |
| 2006/0052704 | A1 | 3/2006 | Baba et al. |
| 2006/0167514 | A1 | 7/2006 | Kjellstrom et al. |
| 2007/0055153 | A1* | 3/2007 | Simopoulos ............. A61B 8/00 600/437 |
| 2009/0105589 | A1* | 4/2009 | Osaka et al. ................... 600/443 |
| 2010/0106213 | A1 | 4/2010 | Hilpisch et al. |
| 2010/0135548 | A1 | 6/2010 | Gerard et al. |
| 2010/0137717 | A1* | 6/2010 | Strand ................... A61B 5/026 600/454 |
| 2010/0234731 | A1 | 9/2010 | Lu et al. |
| 2010/0331700 | A1 | 12/2010 | Baba et al. |
| 2011/0106232 | A1 | 5/2011 | Broome et al. |
| 2012/0022843 | A1 | 1/2012 | Ionasec et al. |

FOREIGN PATENT DOCUMENTS

| | | |
|---|---|---|
| JP | 7148134 A | 6/1995 |
| JP | 2010505494 A | 2/2010 |
| JP | 201224582 A | 2/2012 |
| KR | 1020080091350 A | 10/2008 |

OTHER PUBLICATIONS

Koestenberger et al., "Non-Invasive Imaging for Congential Heart Disease: Recent Innovations in Transthoracic Echocardiography", J Clin Exp Cardiology, Jan. 22, 2012.*

Cruz-Martinez et al., "Learning Curve for Doppler Measurement of fetal modified myocardial performance index", Ultrasound Obstet Gynecol, published online Jan. 14, 2011, pp. 158-162.*

Aase et al., "Automatic Timing of Aortic Valve Closure in Apical Tissue Doppler Images", Ultrasound in Med & Biol., vol. 32, 2006, 19-27.*

Hernandez-Andrade et al., "A modified myocardial performance (Tei) index based on the use of valve clicks improves reproducibility of fetal left cardiac function assessment", Ultsound Obstet Gynecol, 2005, pp. 227-232.*

Sanz et al., "Imaging Techniques and the Evaluation of the Right Heart and the Pulmonary Circulation", Rev. Esp. Cardiol., 2010.*

Correale et al. "Tissue Doppler Imaging in Coronary Artery Diseases and Heart Failure", Current Cardiology Reviews, Published Online Feb. 2012.*

Communication, dated Oct. 24, 2013, issued by the Korean Intellectual Property Office in counterpart Korean Application No. 10-2012-0117913.

Harjai, et al., "The Tei Index: A New Prognostic Index for Patients with Symptomatic Heart Failure", Journal of the American Society of Echocardiography, Sep. 1, 2002, vol. 15, No. 9, pp. 864-868.

Tei, et al., "Doppler Index Combining Systolic and Diastolic Myocardial Performance: Clinical Value in Cardiac Amyloidosis", Journal of the American College of Cardiology, Sep. 1, 1996, vol. 28, No. 3, pp. 658-664.

Extended Search Report dated Jul. 18, 2013, issued by the European Patent Office in counterpart European Patent Application No. 13163808.2.

Communication dated Sep. 3, 2014, issued by the State Intellectual Property Office of P.R. China in counterpart Chinese Application No. 201310136874.5.

M. Ishii et al., "Quantitation of the Global Right Ventricular Function in Children with Normal Heart and Congenital Heart Disease: A Right Ventricular Myocardial Performance Index", Pediatric Cardiology, vol. 21, No. 5, 2000, p. 416-421.

* cited by examiner

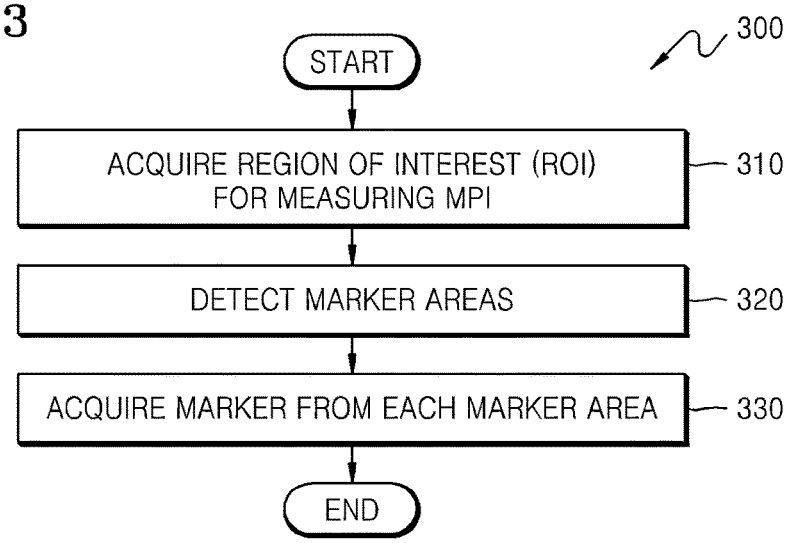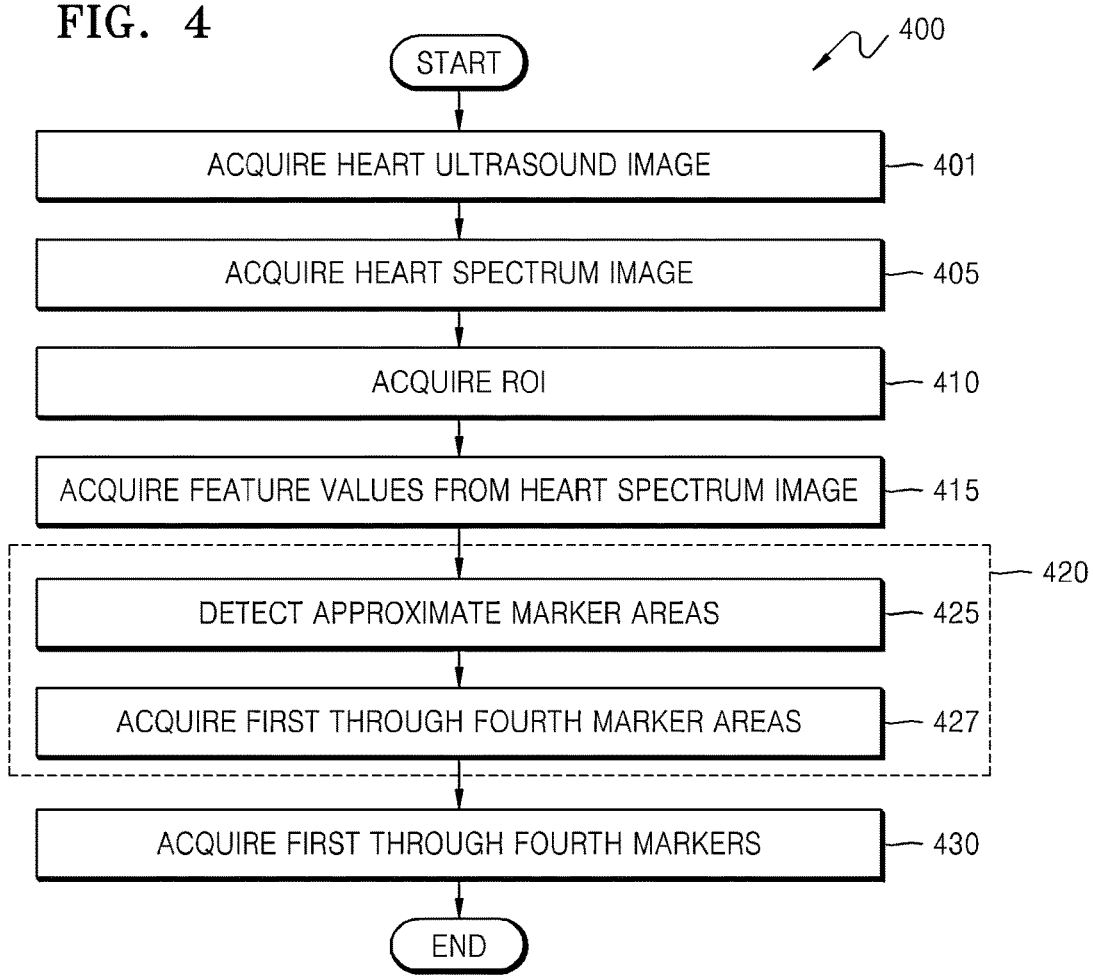

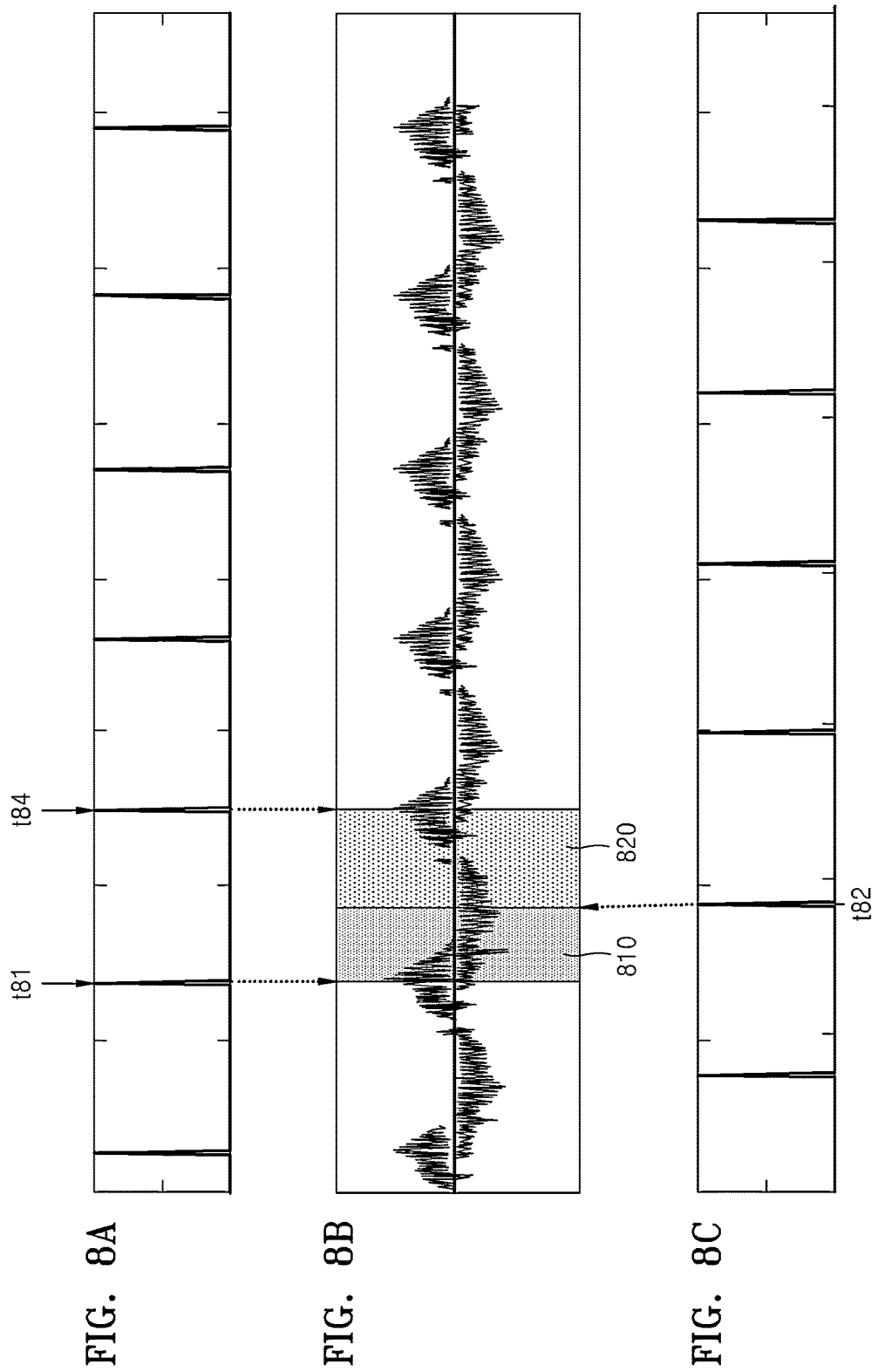

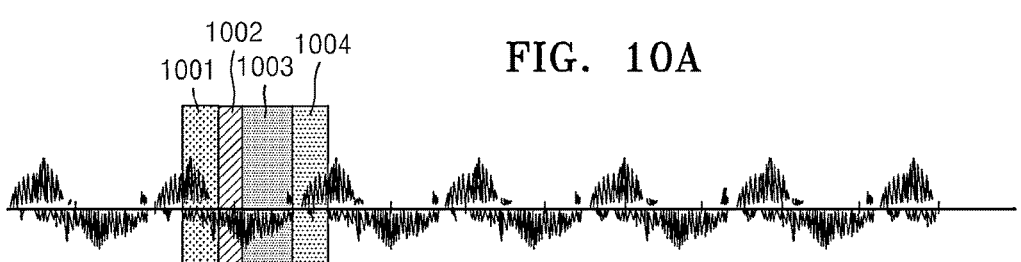
FIG. 10A
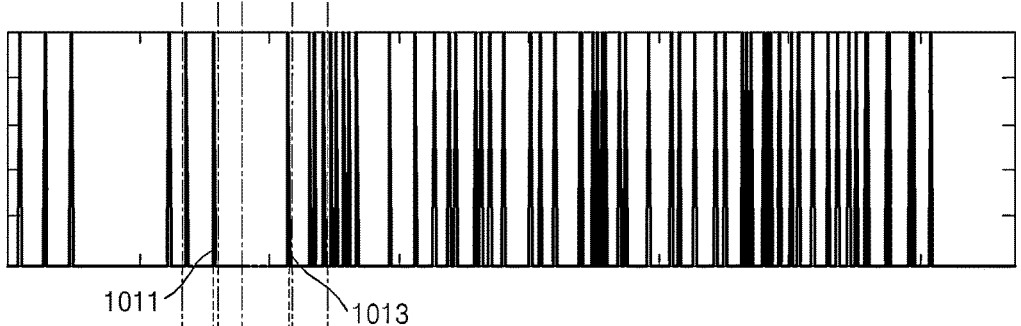
FIG. 10B
FIG. 10C
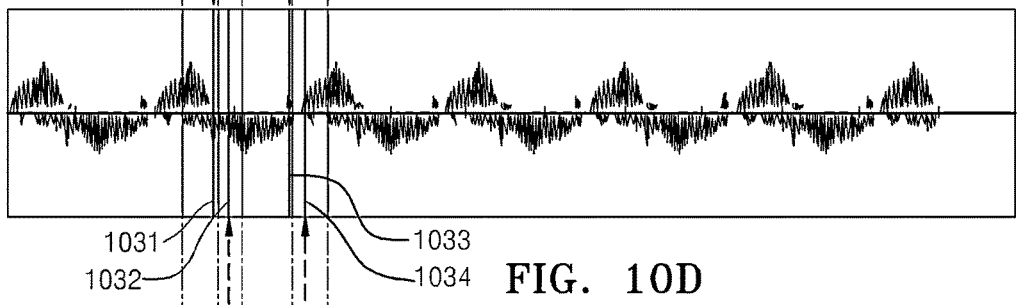
FIG. 10D
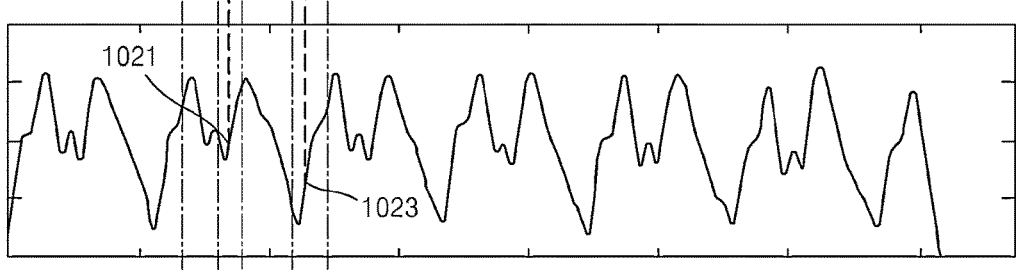

1110  1120  1140
      1130

IMAGE PROCESSING METHOD AND APPARATUS

CROSS-REFERENCE TO RELATED PATENT APPLICATIONS

This application claims priority from U.S. Provisional Application No. 61/635,425, filed on Apr. 19, 2012, in the U.S. Patent and Trademark Office, and claims priority from Korean Patent Application No. 10-2012-0117913, filed on Oct. 23, 2012, in the Korean Intellectual Property Office, the entire disclosures of which are hereby incorporated by reference.

BACKGROUND

1. Field

Methods and apparatuses consistent with exemplary embodiments relate to an image processing method and apparatus, and more particularly, to an image processing method and apparatus for automatically measuring a myocardial performance index (MPI).

2. Description of the Related Art

Ultrasound diagnostic equipment that is widely used to diagnose diseases may reproduce image signals or audio signals corresponding to the bloodstream or heart rate in the human body by using ultrasound. A user, such as a medical practitioner, may diagnose whether a disease has occurred in an organ, such as a heart, by using an ultrasound image generated by ultrasound diagnostic equipment.

For example, in order to diagnose a cardiac disorder of a fetus or an adult, the movement of the fetus's heart or the adult's heart may be observed by using ultrasound diagnostic equipment. In detail, an ultrasound signal is applied to the heart by placing a probe of ultrasound diagnostic equipment in contact with a heart region. Then, a Doppler ultrasound signal that is reflected in response to the applied ultrasound signal, due to a Doppler effect, is received through the probe. The ultrasound diagnostic equipment may acquire an image of the heart's movement by using the received Doppler ultrasound signal.

In order to diagnose whether a heart operates normally, an index of a living body, such as a myocardial performance index (MPI), needs to be measured and it is determined whether the measured index is within a normal range. Although an ultrasound image indicating the movement of the heart has been acquired by using ultrasound diagnostic equipment, a medical practitioner needs to manually analyze the ultrasound image in order to measure an index of the living body, such as the MPI. For example, the medical practitioner may mark points necessary for measuring the MPI on the ultrasound image, and may calculate the MPI by using lengths between each of the marked points.

In this case of passive measurement of the MPI, the accuracy of the calculated result may vary according to the medical practitioner's skill. In addition, if the medical practitioner wrongly marks the points, the MPI may be erroneously calculated.

Accordingly, it is necessary to provide a method and apparatus for more accurately acquiring or obtaining an index of a living body, such as the MPI.

SUMMARY

An exemplary embodiment provides an image processing method and apparatus for measuring a predetermined index of a living body, for example, a myocardial performance index (MPI), by using ultrasound images.

The exemplary embodiment also provides an image processing method and apparatus for accurately measuring an MPI by reducing measurement errors occurring when manually measuring the MPI from ultrasound images.

According to an aspect of the exemplary embodiment, there is provided an image processing method measuring a myocardial performance index (MPI), the image processing method including: obtaining a region of interest (ROI) for measuring the MPI, based on signal levels of an input signal and an output signal of a heart spectrum image; obtaining a plurality of marker areas, within the obtained ROI, wherein at least one marker for measuring the MPI is located, based on a feature value of one of the input signal and the output signal, in each of the plurality of marker areas; and obtaining the at least one marker for each of the plurality of marker areas.

The image processing method may further include obtaining at least one of a peak value corresponding to the input signal and a peak value corresponding to the output signal as the feature value.

The obtaining of the ROI may include: receiving a selection of a predetermined point in the heart spectrum image through a user interface screen; and obtaining a myocardial performance period corresponding to the predetermined point, as the ROI, wherein the obtained myocardial performance period includes one cycle of the input signal and one cycle of the output signal corresponding to the one cycle of the input signal of the heart spectrum image.

The obtaining of the ROI may include obtaining an interval including a plurality of myocardial performance periods as the ROI, wherein each of the plurality of myocardial performance periods include one cycle of the input signal of the heart spectrum image and one cycle of the output signal, corresponding to the one cycle of the input signal.

The obtaining the ROI may include sampling one myocardial performance period which includes one cycle of the input signal and one cycle of the output signal, and using the sampled myocardial performance period as the ROI.

The obtaining of the plurality of marker areas may include: obtaining a first marker area and a second marker area in which a first marker and a second marker are respectively located, a signal interval from a first peak value point corresponding to the input signal to a second peak value point that is adjacent to the first peak value point corresponding to the output signal; and obtaining a third marker area and a fourth marker area in which a third marker and a fourth marker are respectively located, a signal interval from the second peak value point to a third peak value point that is adjacent to the second peak value point corresponding to the input signal.

The obtaining the at least one peak value as the feature value may include cumulating the input signal and the output signal of the heart spectrum image, and using a peak value of at least one of the input signal and the output signal cumulated in the ROI as the feature value.

The obtaining the at least one peak value as the feature value may include high-frequency filtering the heart spectrum image and obtaining a signal peak value of the filtered heart spectrum image as the feature value.

The obtaining the at least one marker may include obtaining the at least one marker for each of the plurality of marker areas based on at least one of a click signal of the input signal and the output signal, a gradient value of the input signal and the output signal, and a signal intensity of the input signal and the output signal.

The image processing method may further include overlaying and displaying the obtained at least one marker on the heart spectrum image.

The obtaining the ROI may include obtaining the ROI based on a maximum signal level of the input signal and a maximum signal level of the output signal.

The image processing method may further include: obtaining a heart ultrasound image captured by using an ultrasound Doppler signal; and obtaining a processed heart ultrasound image by performing at least one of cropping, shifting, and noise reduction on the obtained heart ultrasound image.

The image processing method may further include outputting a user interface screen which sets whether to automatically or manually set the ROI.

The image processing method may further include receiving a selection of a predetermined period of the heart spectrum image or a predetermined point corresponding to the predetermined period of the heart spectrum image and obtaining the predetermined period as the ROI when the manual setting is requested through the user interface screen.

The image processing method may further include obtaining as the ROI an interval, which includes at least one myocardial performance period which includes one cycle of the input signal of the heart spectrum image and one cycle of the output signal corresponding to the one cycle of the input signal, when the automatic setting is requested through the user interface screen.

According to another aspect of the exemplary embodiment, there is provided an image processing apparatus which measures a myocardial performance index (MPI), the image processing apparatus including: a region obtainer which obtains a region of interest (ROI) to measure the MPI, based on signal levels of an input signal and an output signal of a heart spectrum image and which obtains from the ROI, a plurality of marker areas, wherein at least one marker which measures the MPI is located in each of the plurality of marker areas, based on a feature value of at least one of the input signal and the output signal; and a marker obtainer which obtains the at least one marker for each of the plurality of marker areas.

The region obtainer may include: a feature value extractor which obtains at least one of a peak value corresponding to the input signal and a peak value corresponding to the output signal as the feature value; and a marker region obtainer which obtains the plurality of marker areas based on the feature value.

The image processing apparatus may further include: a user interface which receives a selection of a predetermined point in the heart spectrum image; and an ROI obtainer which obtains as the ROI a myocardial performance period corresponding to the predetermined point, wherein the myocardial performance period includes one cycle of the input signal of the heart spectrum image and one cycle of the output signal corresponding to the one cycle of the input signal.

The image processing apparatus may further include an ROI obtainer which obtains as the ROI an interval including a plurality of myocardial performance periods, wherein each of the plurality of myocardial performance periods includes one cycle of the input signal of the heart spectrum image and one cycle of the output signal of the heart spectrum image corresponding to the one cycle of the input signal.

The image processing apparatus may further include an ROI obtainer which samples one myocardial performance period which includes one cycle of the input signal and one cycle of the output signal and which uses the sampled myocardial performance period as the ROI.

The marker region obtainer may obtain a first marker area and a second marker area in which a first marker and a second marker are respectively located, a signal interval from a first peak value point corresponding to the input signal to a second peak value point that is adjacent to the first peak value point corresponding to the output signal, and may obtain third marker area and a fourth marker area in which a third marker and a fourth marker are respectively located, a signal interval from the second peak value point to a third peak value point that is adjacent to the second peak value point corresponding to the input signal.

The feature value extractor may cumulate the input signal and the output signal of the heart spectrum image and may use a peak value of at least one of the input signal and the output signal cumulated in the ROI as the feature value.

The feature value extractor may high-frequency filter the heart spectrum image and may obtain a signal peak value of the filtered heart spectrum image as the feature value.

The marker obtainer may obtain the at least one marker for each of the plurality of marker areas, based on at least one of a click signal of the input signal and the output signal, a gradient value of the input signal and the output signal, and a signal intensity of the input signal and the output signal.

The image processing apparatus may further include an inputter/outputter which overlays and displays the obtained at least one marker on the heart spectrum image.

The image processing apparatus may further include an image obtainer which obtains a heart ultrasound image captured by using an ultrasound Doppler signal and which obtains a processed heart ultrasound image by performing at least one of cropping, shifting, and noise reduction on the obtained heart ultrasound image.

The image processing apparatus may further include: a user interface which outputs a user interface screen for setting whether to automatically or manually set the ROI; and an ROI obtainer which obtains the ROI.

When the manual setting is requested through the user interface screen, the ROI obtainer may receive a selection of a predetermined period of the heart spectrum image or a predetermined point corresponding to the predetermined period and may obtain the predetermined period as the ROI.

When the automatic setting is requested through the user interface screen, the ROI obtainer may acquire as the ROI an interval, which includes at least one myocardial performance period which includes one cycle of the input signal of the heart spectrum image and one cycle of the output signal corresponding to the one cycle of the input signal.

BRIEF DESCRIPTION OF THE DRAWINGS

The above and other features of the exemplary embodiments will become more apparent by describing in detail exemplary embodiments thereof with reference to the attached drawings in which:

FIG. 3 is a flowchart illustrating an image processing method according to an exemplary embodiment;

FIG. 4 is a flowchart illustrating an image processing method according to another exemplary embodiment;

FIGS. 8A through 8C are diagrams for explaining operation 425 of FIG. 4;

FIGS. 10A through 10D are diagrams for explaining operation 430 of FIG. 4;

DETAILED DESCRIPTION

Hereinafter, a method and apparatus for processing an image according to an exemplary embodiment are described in detail with reference to attached drawings.

Expressions such as "at least one of," when preceding a list of elements, modify the entire list of elements and do not modify the individual elements of the list.

Figure 1:
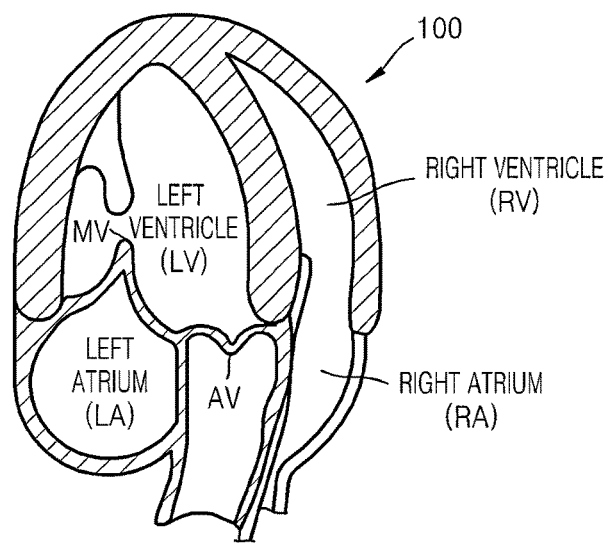
FIG. 1 is a diagram illustrating a heart as a target for ultrasound measurement.

FIG. 1 is a diagram illustrating a heart 100 as a target for performing ultrasound measurement.

Referring to FIG. 1, the heart 100 may be divided into a left ventricle (LV) 101, a left atrium (LA) 102, a right ventricle (RV) 103, and a right atrium (RA) 104.

Blood flows into and out of the heart 100 when a mitral valve (MV) 105 and an aortic valve (AV) 106 are opened and/or closed.

A heart spectrum image or a spectral image of a heart, through which the flow of blood flowing into and out of the heart 100 may be observed, may be acquired or obtained by using an ultrasound Doppler signal which is a signal reflected from the heart in response to an ultrasound signal which was applied to the heart 100. A medical practitioner, such as a doctor, or ultrasound technician, may diagnose whether the heart has an abnormality by analyzing the heart spectrum image indicating the flow of blood, which corresponds to a movement of the heart 100.

The heart spectrum image is described in detail with reference to FIG. 2 below.

Figure 2:
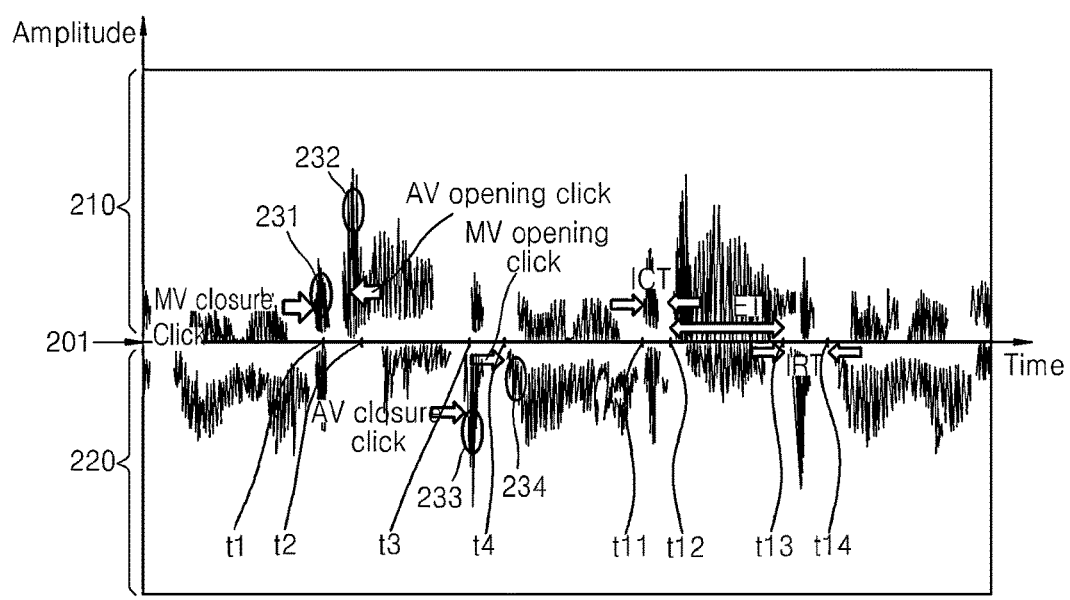
FIG. 2 is a diagram illustrating a heart spectrum image or a spectral image of a heart.

FIG. 2 is a diagram illustrating a heart spectrum image. In FIG. 2, the x-axis indicates time and the y-axis indicates the amplitude of the ultrasound signal.

Referring to FIG. 2, with respect to a base line 201, the inflow of blood is illustrated in an upper part 210 and the outflow of blood the heart is illustrated in a lower part 220. Hereinafter, an image that indicates both the inflow and the outflow of blood is referred to as a heart spectrum image. The graph in the upper part 210 that indicates the inflow of blood is referred to as an input signal, and the graph in the lower part 220 that indicates the outflow of blood is referred to as an output signal.

In general, in order to determine whether a heart is moving normally, a myocardial performance index (MPI), that is, a living body index, may be measured to determine whether the measured MPI is within a normal range. The normal range can be determined based on, for example, a range determined by the medical profession. The MPI is a value obtained by marking a start or end time point on each of the flows of the input signal and the output signal in the heart spectrum image and quantifying intervals between each of the marked time points according to a predetermined equation. A medical practitioner, such as a doctor, or an ultrasound technician, may determine whether the heart of a patient moves normally by using the MPI value of the patient.

The MPI may be calculated by Equation 1.

$$MPI=(ICT+IRT)/ET=(MCT-ET)/ET \tag{1}$$

ICT in Equation 1 denotes an isovolumic contraction time (ICT). The ICT is the time from a closure end time point t1 of an AV to an opening start time point t2 of an MV.

IRT in Equation 1 denotes an isovolumic relaxation time (IRT). The IRT is the time from a closure end time point t3 of the MV to an opening start time point t4 of the AV.

ET in Equation 1 denotes an ejection time (ET), and is the time between the ICT and the IRT.

MCT in Equation 1 denotes a mitral closure time (MCT), and is an interval between the end point of an inflow bloodstream of the MV and the start point of the inflow bloodstream of the MV. For example, the MCT may be one period of the input signal of FIG. 2.

For example, in order to measure the ICT, the IRT, and the ET, which are necessary to calculate the MPI, the closure end time point t1 of the AV, the opening start time point t2 of the MV, the closure end time point t3 of the MV, and the opening start time point t4 of the AV need to be known. In the conventional art, a medical practitioner manually marks the time points t1 to t4 on the input signal and the output signal of the heart spectrum image, and manually calculates the MPI by using the manually marked time points t1 to t4.

In FIG. 2, t11, t12, t13, and t14 respectively correspond to the closure end time point t1 of the AV, the opening start time point t2 of the MV, the closure end time point t3 of the MV, and the opening start time point t4 of the AV.

In order to measure the MPI by using an ultrasound image captured from the heart, generally, a medical practitioner, for example, needs to manually mark at least four time points for measuring the MPI. That is, the medical practitioner must mark time points t1 to t4, on the heart spectrum image. The heart spectrum image is a type of heart ultrasound image.

Visually reading and determining the time points t1 to t4 on the heart spectrum image may cause an error or a mistake according to the medical practitioner's level of skill and based on the amount of noise components included in the heart spectrum image.

In the exemplary embodiment, the MPI may be measured by first acquiring marker areas where the time points t1, t2, t3, and t4 necessary to measure the MPI are located and by detecting markers corresponding to the time points t1, t2, t3, and t4 in the marker areas. Based on the foregoing, the MPI may be measured automatically instead of requiring a medical practitioner to mark each of the time points.

FIG. 3 is a flowchart illustrating an image processing method 300 according to an exemplary embodiment.

Referring to FIG. 3, the image processing method 300 for measuring an MPI includes acquiring a region of interest (ROI) for measuring the MPI, based on signal levels of an input signal and an output signal in a heart spectrum image (operation 310).

In detail, the heart spectrum image corresponds to an ultrasound image illustrated in FIG. 2, and the input signal and the output signal correspond to a signal illustrated in the upper part 210 above the base line 201 and a signal illustrated in the lower part 220 under the base line 201, respectively. In addition, the ROI indicates a predetermined section of the heart spectrum image, sampled to measure the MPI. That is, the MPI is measured by using and/or analyzing the input signal and the output signal of the heart spectrum image, which are included in the ROI.

A plurality of marker areas where a plurality of markers for measuring the MPI are located are acquired or obtained from the ROI acquired based on feature values of the input signal and the output signal in the ROI acquired in operation 310 (operation 320).

In detail, each marker may indicate each point in the heart spectrum image which is necessary to calculate the MPI, or the position of each point in the heart spectrum image which is necessary to obtain time intervals between each point. For example, each marker may correspond to at least one of the closure end time point t1 of the AV, the opening start time point t2 of the MV, the closure end time point t3 of the MV, and the opening start time point t4 of the AV, which are necessary to measure the ICT, the IRT, and the ET, as described with respect to FIG. 2.

Each marker area indicates an area where a marker is likely to be located. A marker area is described in detail with reference to FIGS. 8 and 9 below.

At least one marker is acquired for each of the plurality of marker areas detected in operation 320 (operation 330). In detail, after acquiring each limited area by limiting each marker area, each marker may be accurately sensed within each limited marker area and acquired.

FIG. 4 is a flowchart illustrating an image processing method 400 according to another exemplary embodiment.

Operations 410, 420, and 430 illustrated in FIG. 4 respectively correspond to operations 310, 320, and 330 illustrated in FIG. 3. Accordingly, descriptions overlapping with those of FIG. 3 are omitted. The image processing method 400 may further include at least one of operations 401, 405, and 415, compared to the image processing method 300 of FIG. 3.

Referring to FIG. 4, the image processing method 400 may further include acquiring a heart ultrasound image (operation 401). In detail, the heart ultrasound image may be an image captured based on an ultrasound Doppler signal that is a reflection signal received from the heart of a patient after applying an ultrasound signal to a heart area. The ultrasound signal may be applied by, for example, an ultrasound transducer or probe. The heart ultrasound image may be captured by an ultrasound image capture apparatus (not shown). The ultrasound image capture apparatus can be, for example, any ultrasound machine or device which can create an ultrasound image. The heart ultrasound image may be raw data including noise. Also, the heart ultrasound image may be externally obtained. For example, a previously obtained ultrasound image may be provided. In addition, the heart ultrasound image may be autonomously generated by receiving an ultrasound Doppler signal from the heart of a patient after transmitting an ultrasound signal to the heart area of the patient. The heart ultrasound image is described in further detail with reference to FIG. 5 below.

The image processing method 400 may further include acquiring a heart spectrum image by performing image-processing on the heart ultrasound image acquired in operation 401 (operation 405).

In detail, the heart spectrum image may be acquired by performing at least one of cropping, shifting, and noise reduction with respect to the heart ultrasound image. If the noise reduction processing is not performed, markers may not be accurately acquired due to errors of signal values existing in the heart spectrum image because of the noise. Accordingly, after acquiring a heart spectrum image accurately indicating the movement of a heart by reducing signal noises through preprocessing, more accurate marker detection may be performed with respect to the acquired heart spectrum image.

Figure 5:
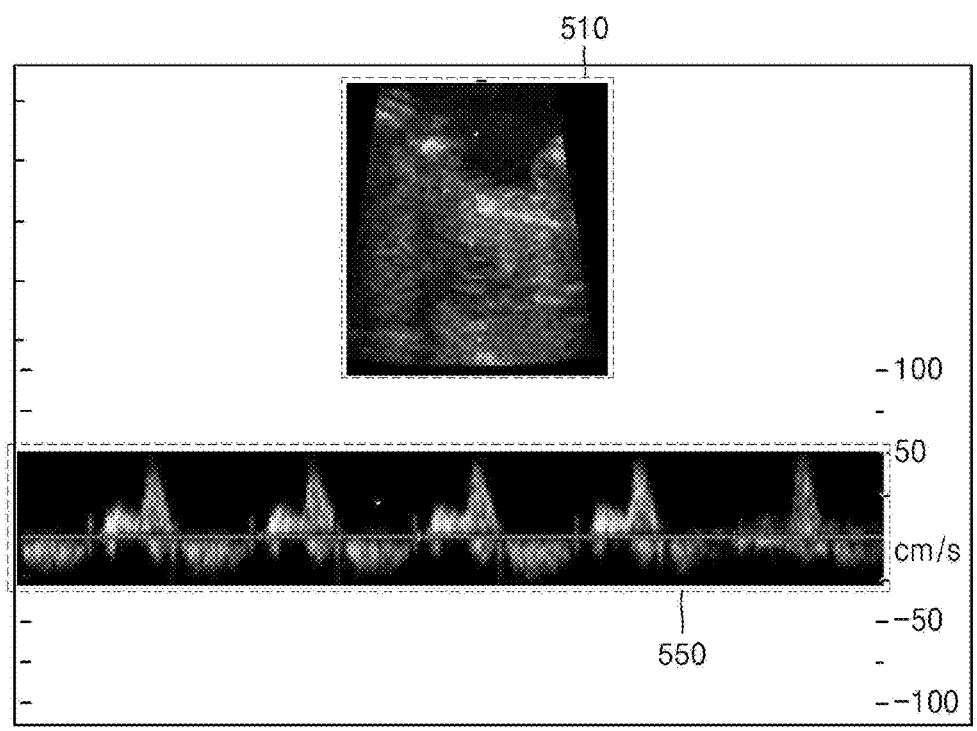
FIG. 5 is a diagram illustrating a heart ultrasound image.

FIG. 5 is a diagram illustrating a heart ultrasound image.

Referring to FIG. 5, an ultrasound image 510 indicating the movement of a heart itself may be acquired by using an ultrasound image capture apparatus (not shown). An ultrasound image capture apparatus can be, for example, any ultrasound machine or device which can create an ultrasound image. In addition, an ultrasound image 550 indicating the inflow and outflow of blood in the heart, which indicates the movement of the heart, may be acquired.

The ultrasound image 510 and/or ultrasound image 550 illustrated in FIG. 5 may be raw data or an image on which image preprocessing has been performed. The ultrasound image 510 and/or ultrasound image 550 may be displayed on a display device (not shown) to be watched by a user such as a patient, a medical practitioner, or the like. The display device can include, for example, an HD Liquid Crystal Display (LCD) monitor, an LCD monitor, or a touch screen display. Such display devices are examples and the exemplary embodiments are not limited to these display devices. Further, the ultrasound image can be displayed in black and white or in color. The ultrasound image 550 corresponds to the heart spectrum image illustrated in FIG. 2.

The image processing method 400 may include acquiring an ROI from the heart spectrum image (operation 410).

For example, the ROI may be manually set by a user or may be autonomously set in the image processing method 400. An exemplary operation in which a user manually sets the ROI is described in detail with reference to FIG. 6 below.

Figure 6:
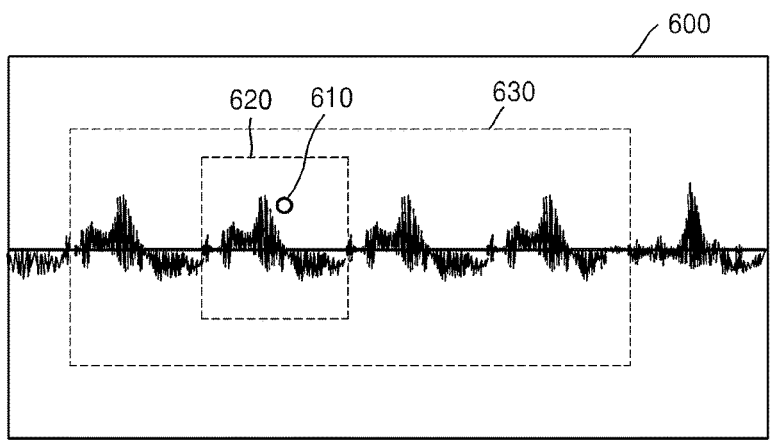
FIG. 6 is a diagram illustrating a heart spectrum image.

FIG. 6 is another diagram illustrating a heart spectrum image.

Referring to FIG. 6, a user interface screen, such as a computer display or monitor, including a heart spectrum image 600 indicating the inflow and outflow of blood in a heart is illustrated. The heart spectrum image 600 corresponds to the ultrasound image 550 illustrated in FIG. 5.

The acquiring of the ROI (operation 410) may include receiving a selection of a predetermined point in the heart spectrum image through the user interface screen and acquiring a myocardial performance period corresponding to the predetermined point as the ROI. The selection of the predetermined point may be made by a user, such as a medical practitioner. The acquired myocardial performance period includes one cycle of the input signal and one cycle of the output signal corresponding to the one cycle of the input signal of the heart spectrum image. When a predetermined point 610 of the heart spectrum image 600 included in the user interface screen is selected, one myocardial performance cycle 620, where the predetermined point 610 is positioned, may be acquired as the ROI. For example, when a medical practitioner clicks the predetermined point 610, using for example, a mouse, a keyboard or other selection device, it may be determined that the predetermined point 610 is selected.

In addition, when a predetermined point 610 of the heart spectrum image 600 included in the user interface screen is selected, a plurality of myocardial performance cycles 630 centered around the predetermined point 610 may be acquired as the ROI. FIG. 6 illustrates an example in which four myocardial performance cycles centered around the predetermined point 610 are acquired as the ROI.

An operation of acquiring the ROI may be performed in the image processing method 400 without a selection operation of a user.

In the acquiring of the ROI (operation 410), an interval including a plurality of myocardial performance periods may be acquired as the ROI, and each myocardial performance period includes one cycle of the input signal and one cycle of the output signal corresponding to the one cycle of the input signal of the heart spectrum image.

For example, when the plurality of myocardial performance periods are acquired as the ROI, markers may be acquired for each myocardial performance period. In this case, each MPI may be calculated for each myocardial performance period by using the markers, and an average value of MPIs of the plurality of myocardial performance period may be acquired as a final MPI.

In addition, in the acquiring of the ROI (operation 410), one myocardial performance period, for example, the myocardial performance period 620, which includes one cycle of the input signal of the heart spectrum image 600 and one cycle of the output signal of the heart spectrum image 600 may be sampled, and the sampled myocardial performance period may be acquired as the ROI. In this case, the MPI may be finally acquired by using markers acquired from the one myocardial performance period.

In addition, in the acquiring of the ROI (operation 410), the ROI may be acquired based on a maximum signal level of the input signal and a maximum signal level of the output signal. In detail, an interval from a point corresponding to the maximum level of the input signal to a point corresponding to a next maximum signal level of the input signal may be determined as one myocardial performance period and the myocardial performance period may be acquired as the ROI. In addition, an interval from a point corresponding to the maximum level of the output signal to a point corresponding to a next maximum signal level of the output signal may be determined as one myocardial performance period and the myocardial performance period may be acquired as the ROI.

The acquiring of the ROI (operation 410) may further include providing the user interface screen for setting whether to automatically or manually set the ROI. Accordingly, a user may determine whether to automatically or manually set the ROI, and the automatic setting or manual setting may be performed according to the user's decision. When the manual setting is requested through the user interface screen, as described with reference to FIG. 6, a predetermined cycle or a predetermined point corresponding to the predetermined cycle of the heart spectrum image may be selected and the predetermined cycle may be acquired as the ROI. When the automatic setting is requested through the user interface screen, an interval including at least one myocardial performance period which includes one cycle of the input signal of the heart spectrum image and one cycle of the output signal corresponding to the one cycle of the input signal may be acquired as the ROI.

The image processing method 400 may further include acquiring a plurality of feature values from the heart spectrum image (operation 415). In detail, at least one of a peak value corresponding to the input signal and a peak value corresponding to the output signal may be acquired as the feature values. An operation of acquiring the feature values is described in detail with reference to FIGS. 7A through 7D below.

FIGS. 7A through 7D are diagrams for explaining a conversion signal of a heart spectrum image which is used to acquire the feature values.

Figure 7A:
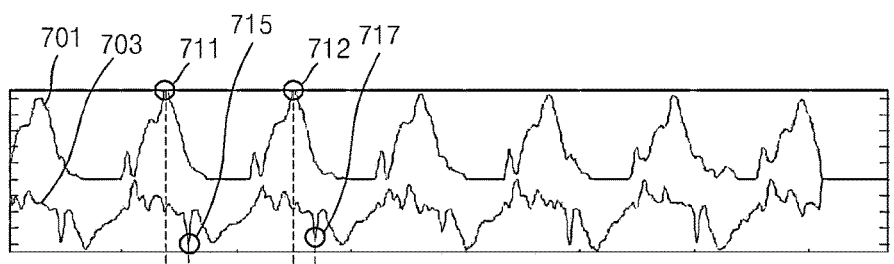
FIGS. 7A through 7D are diagrams for explaining a conversion signal of a heart spectrum image that is used to acquire or obtain feature values.
Figure 7B:
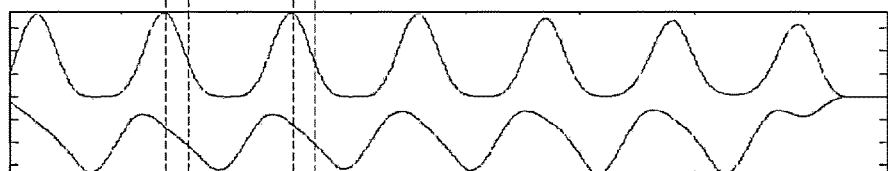
Figure 7C:
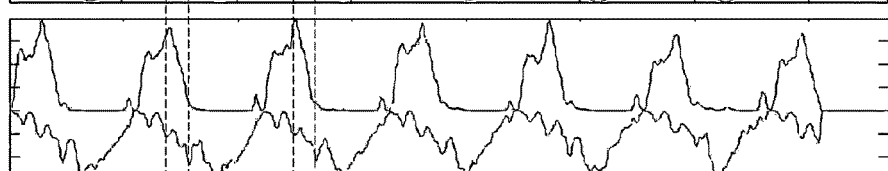

FIG. 7A illustrates a binarized cumulative signal obtained by binarizing the input signal and output signal included in the heart spectrum image and cumulating the binarized input signal and output signal for each cycle. FIG. 7B illustrates a morphological signal obtained by cancelling noise in the input signal and output signal of the heart spectrum image and then cumulating the noise-cancelled input signal and output signal for each cycle. FIG. 7C illustrates a gray signal obtained by cumulating gradation values of the input signal and the output signal of the heart spectrum image.

Figure 7D:
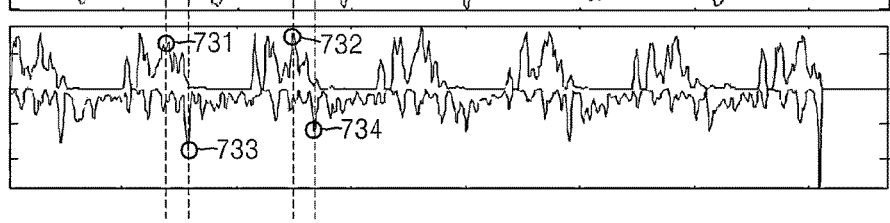

FIG. 7D illustrates a signal obtained by converting the input signal and output signal included in the heart spectrum image to a frequency domain. In detail, the signal illustrated in FIG. 7D may be a signal obtained by converting the heart spectrum image by using a conversion for leaving only high frequency components in the heart spectrum image or by using a conversion for filtering only the high frequency components in the heart spectrum image.

That is, a signal obtained by Laplace transformation of the input single and output signal included in the heart spectrum image is illustrated in FIG. 7D. A Laplace transform is an integral transform which resolves a function into its moments, which are a quantitative measure of the shape of a set of points.

Cumulative signals obtained by cumulating the input signal and the output signal included in the heart spectrum image may be used to acquire the feature values. In detail, the signals illustrated in FIGS. 7A, 7B, and 7C may be used to acquire the feature values.

For example, the input signal and output signal of the heart spectrum image may be cumulated, and a peak value of at least one of the input signal (for example, 701) cumulated in an ROI and a peak value (for example, 703) of the output signal cumulated in the ROI may be acquired as the feature values. Therefore, the feature values can be a peak value of an input signal or an output signal. For example, in FIG. 7A, time points or points in the heart spectrum image, which correspond to peak value 711 and peak value 712 of a cumulated input signal, may be acquired as the feature values. In addition, time points or points in the heart spectrum image, which correspond to peak value 715, and peak value 717 of a cumulated output signal, may be acquired as the feature values.

A signal obtained by converting the domain of the input signal and the output signal included in the heart spectrum image to the frequency domain or a signal obtained by high-frequency filtering the input signal and the output signal included in the heart spectrum image may be used to acquire the feature values. In detail, a signal illustrated in FIG. 7D may be used to acquire the feature values.

That is, in operation 415, the heart spectrum image may be high-frequency filtered, and signal peak values of the filtered heart spectrum image may be acquired as the feature values. For example, in FIG. 7D, time points or points in the heart spectrum image, which correspond to peak value 731 and peak value 732 of a cumulated input signal, may be acquired as the feature values. In addition, time points or points in the heart spectrum image, which correspond to peak value 733 and peak value 734 of a cumulated output signal, may be acquired as the feature values. Peak value 731 and peak value 732 may be acquired at the same time points or points as peak value 711 and peak value 712, respectively, and peak value 733 and peak value 734 may be acquired at the same time points or points as peak value 715 and peak value 717, respectively.

In the image processing method 400, the acquiring of the marker areas (operation 420) may include detecting approximate marker areas (operation 425) and acquiring detailed marker areas in the approximate marker areas (operation 427).

For example, in order to acquire as markers the closure end time point t1 of the AV, the opening start time point t2 of the MV, the closure end time point t3 of the MV, and the opening start time point t4 of the AV, which are necessary to measure the MPI, as described above with reference to FIG. 2, four marker areas need to be acquired in one myocardial performance period. The markers can be, for example, indicators of the closure end time point t1 of the AV, the opening start time point t2 of the MV, the closure end time point t3 of the MV, and the opening start time point t4 of the AV.

For convenience, the case where four marker areas are acquired in one myocardial performance period and markers are acquired for each marker area is described as an example with reference to FIGS. 8A through 8C below.

FIGS. 8A through 8C are diagrams for explaining operation 425 of FIG. 4. FIG. 8A illustrates peak values detected in a signal, for example, the cumulative signal 701 of the binarized input signal, corresponding to the input signal of the heart spectrum image, in FIG. 7A. FIG. 8B is a diagram illustrating the heart spectrum image. FIG. 8C illustrates peak values detected in a signal, for example, the cumulative signal 703 of the binarized output signal, corresponding to the output signal of the heart spectrum image, in FIG. 7A.

Referring to FIG. 8B, a predetermined area including area 810 and area 820 may be set as the ROI.

Referring to FIGS. 8A to 8C, a peak value point t81, a peak value point t82, and a peak value point t84 correspond to the points, respectively, where the peak value 711 corresponding to the input signal, the peak value 733 corresponding to the output signal, and the peak value 712 corresponding to the input signal have been detected in FIGS. 7A to 7D. Below, for convenience of explanation, the peak value point t81, the peak value point t82, and the peak value point t84 are respectively referred to as a first peak value point, a second peak value point, and a third peak value point.

In operation 425, approximate marker areas may be acquired by using the peak values that are the feature values acquired in operation 415. In detail, a signal interval from the first peak value point t81 corresponding to the input signal to the second peak value point t82 that is adjacent to the first peak value point t81 and corresponds to the output signal may be acquired as a first and second marker area 810 in which first and second markers exist.

In addition, a signal interval from the second peak value point t82 to the third peak value point t84 that is adjacent to the second peak value point t82 and corresponds to the input signal may be acquired as a third and fourth marker area 820 in which third and fourth markers exist.

After acquiring approximate marker area 810 and approximate marker area 820 in operation 425, detailed marker areas may be acquired for each of marker area 810 and marker area 820 acquired in operation 425 (operation 427).

FIGS. 9A through 9D are diagrams for explaining operation 427 of FIG. 4.

Figure 9A:
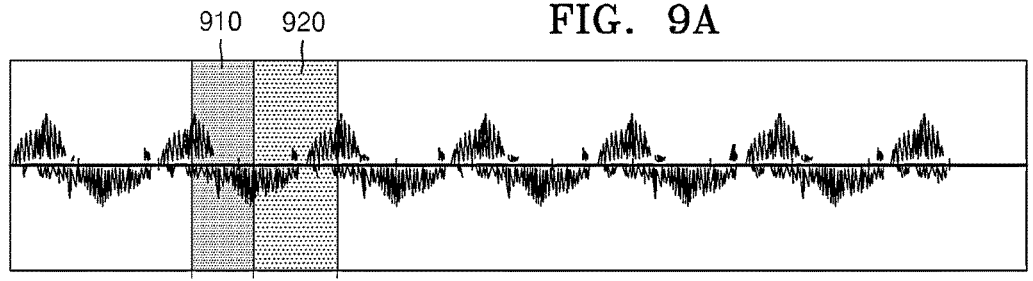
FIGS. 9A through 9D are diagrams for explaining operation 427 of FIG. 4.

FIG. 9A corresponds to FIG. 8B and shows approximate marker area 910 and approximate marker area 920. Approximate marker area 910 and approximate marker area 920 correspond to approximate marker area 810 and approximate marker area 820 illustrated in FIG. 8B, respectively.

Figure 9B:
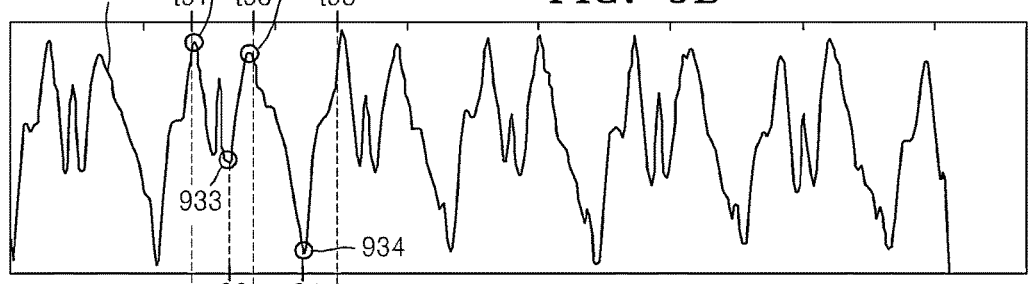
Figure 9C:
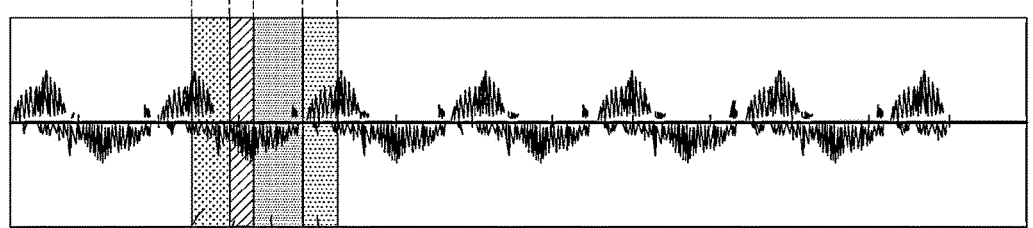
Figure 9D:
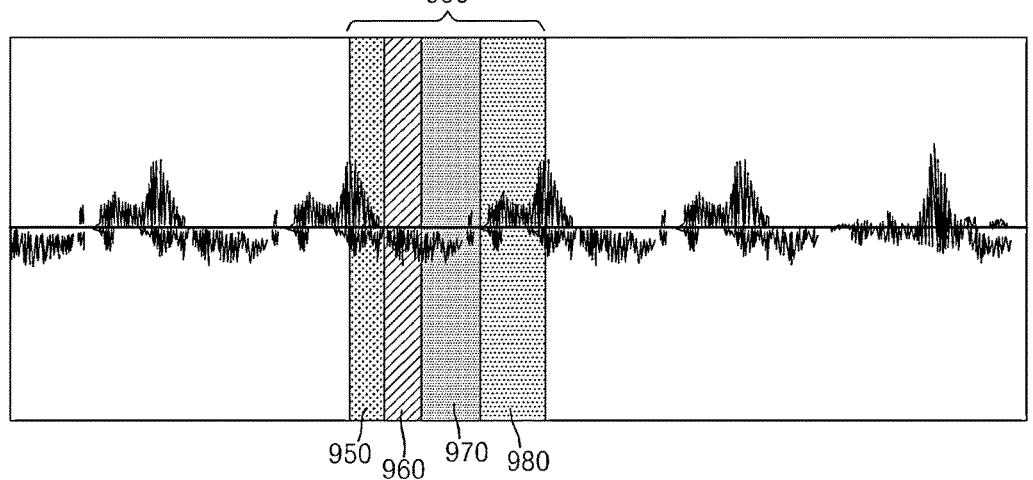

FIG. 9B is a diagram illustrating a normalized summation signal 930 of a cumulative signal described with reference to FIGS. 7A, 7B, and 7C. FIG. 9C is a diagram illustrating detailed marker areas. FIG. 9D is a diagram illustrating an image displayed by overlaying the detailed marker areas on a heart spectrum image.

Referring to FIGS. 9A through 9C, the detailed marker areas may be defined based on an upper peak value 931 and an upper peak value 932, and lower peak value 933 and lower peak value 934, which are detected in the normalized summation signal 930. In detail, the first marker area 910 may be divided into a first marker area 950 and a second marker area 960 and the second marker area 920 may be divided into a third marker area 970 and a fourth marker area 980, based on points t91, t92, t93, t94, and t95 where each peak value is located.

That is, the first marker area 910 may be divided into the first marker area 950 and the second marker area 960 based on the point t92 where the lower peak value 933 of the normalized summation signal 930 is located. Thus, the first marker area 950 and the second marker area 960 may be obtained, and a first marker and a second marker may be detected in the first marker area 950 and the second marker area 960, respectively.

In addition, the marker area 920 is divided into the third marker area 970 and the fourth marker area 980 based on the point t94 where the lower peak value 934 of the normalized summation signal 930 are located. Thus, the third marker area 970 and the fourth marker area 980 may be obtained, and a third marker and a fourth marker may be detected in the third marker area 970 and the fourth marker area 980, respectively.

Referring to FIG. 9D, an image obtained by overlying the obtained first marker area 950, second marker area 960, third marker area 970, and fourth marker area 980 on the heart spectrum image may be displayed to a user. An ROI 990 may be additionally displayed on the displayed image.

Next, each marker is acquired for each marker area acquired in operation 420 (operation 430).

In detail, in operation 430, each marker may be acquired for each marker area based on at least one of a click signal of the input signal and the output signal, a gradient value of the input signal and the output signal, and a signal intensity of the input signal and output signal.

FIGS. 10A through 10D are diagrams for explaining operation 430 of FIG. 4.

FIG. 10A is a diagram illustrating a heart spectrum image including first marker area 1001, second marker area 1002, third marker area 1003, and fourth marker area 1004 acquired in operation 427. FIG. 10B is a diagram illustrating a click signal existing in an image spectrum signal. FIG. 10C is a diagram illustrating a marker, detected by using the click signal and a gradient value of the input signal and output signal. FIG. 10D is a diagram illustrating a normalized cumulative signal of the heart spectrum image.

Referring back to FIG. 2, in the heart spectrum image, a click signal may be generated when the MV or the AV is opened or closed. For example, a click signal 231 may be generated when the MV is closed, and a click signal 232 may be generated when the AV is opened. In addition, a click signal 233 may be generated when the AV is closed, and a click signal 234 may be generated when the MV is opened.

Accordingly, a point on a click signal, which is detected in each of the first marker area 1001, second marker area 1002, third marker area 1003, and fourth marker area 1004, may be detected as a marker point.

In detail, a first marker 1031 may be acquired at a detection point of a click signal 1011 that was detected in the first marker area 1001. A third marker 1033 may be acquired at a detection point of a click signal 1013 that was detected in the third marker area 1003.

In addition, point 1021 and point 1023 having a maximum gradient value may be detected and markers may be acquired at detected point 1021 and detected point 1023 in a graph illustrating the normalized cumulative signal of the input signal and the output signal of the heart spectrum image, illustrated in FIG. 10D. In detail, a second marker 1032 may be acquired in the maximum gradient point 1021 existing in the second marker area 1002. A fourth marker 1034 may be acquired at the maximum gradient point 1023 located in the fourth marker area 1004.

In the image processing method 400, the MPI may be calculated by using the points of the markers acquired in operation 430.

The image processing method 400 may further include overlaying and displaying (not shown) the acquired markers on the heart spectrum image after operation 430.

Figure 11:
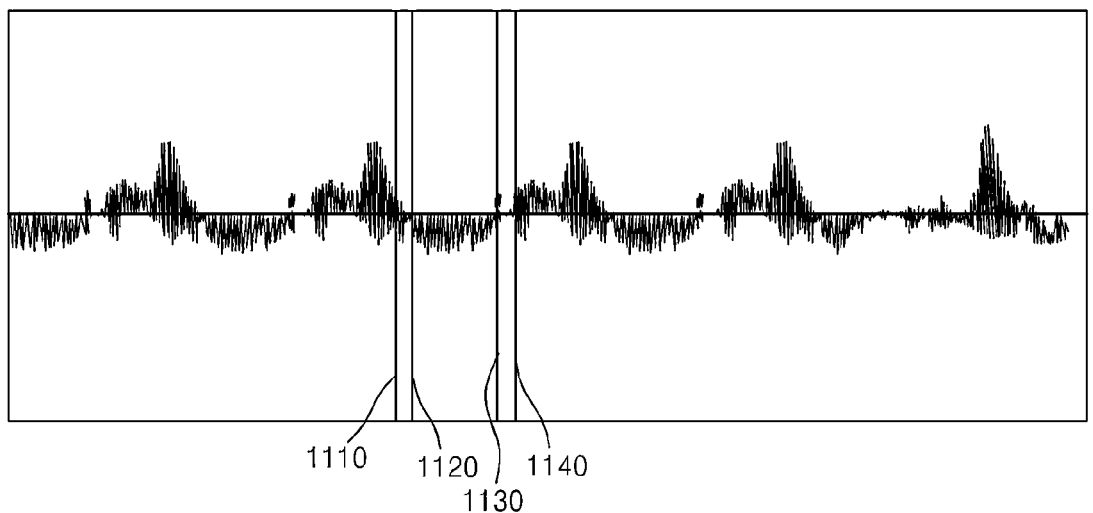
FIG. 11 is a diagram illustrating a heart spectrum image that is displayed.

FIG. 11 is a diagram illustrating a heart spectrum image that is displayed to a user on, for example, a computer display.

Referring to FIG. 11, a first marker 1110, a second marker 1120, a third marker 1130, and a fourth marker 1140 acquired in operation 430 may be indicated in the heart spectrum image, and then the heart spectrum image may be displayed to a user.

Figure 12:
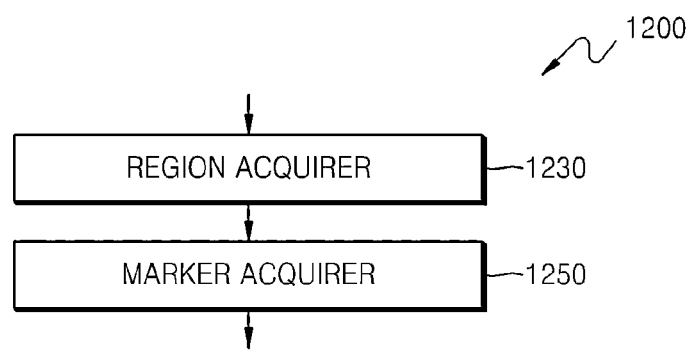
FIG. 12 is a block diagram of an image processing apparatus according to an exemplary embodiment.

FIG. 12 is a block diagram of an image processing apparatus 1200 according to an exemplary embodiment. Operations of the image processing apparatus 1200 illustrated in FIG. 12 are partially the same as the operations of the image processing method 300 or image processing method 400 described with reference to FIGS. 1 through 11 according to an exemplary embodiment. Accordingly, descriptions overlapping with those of FIGS. 1 through 11 are not repeated.

Referring to FIG. 12, the image processing apparatus 1200 includes a region acquirer 1230 and a marker acquirer 1250. Below, a detailed operation of the image processing apparatus 1200 is described with reference to the image processing method 300.

The region acquirer 1230 acquires a ROI for measuring an MPI based on signal levels of the input signal and output signal of the heart spectrum image, and acquires from the ROI a plurality of marker areas. In each of the acquired plurality of marker areas, at least one marker for measuring the MPI is located, based on feature values of the input signal and output signal. That is, the region acquirer 1230 performs operation 310 and operation 320 of the image processing method 300.

The marker acquirer 1250 acquires at least one marker for each of the acquired plurality of marker areas. That is, the marker acquirer 1250 performs operation 330 of the image processing method 300.

Figure 13:
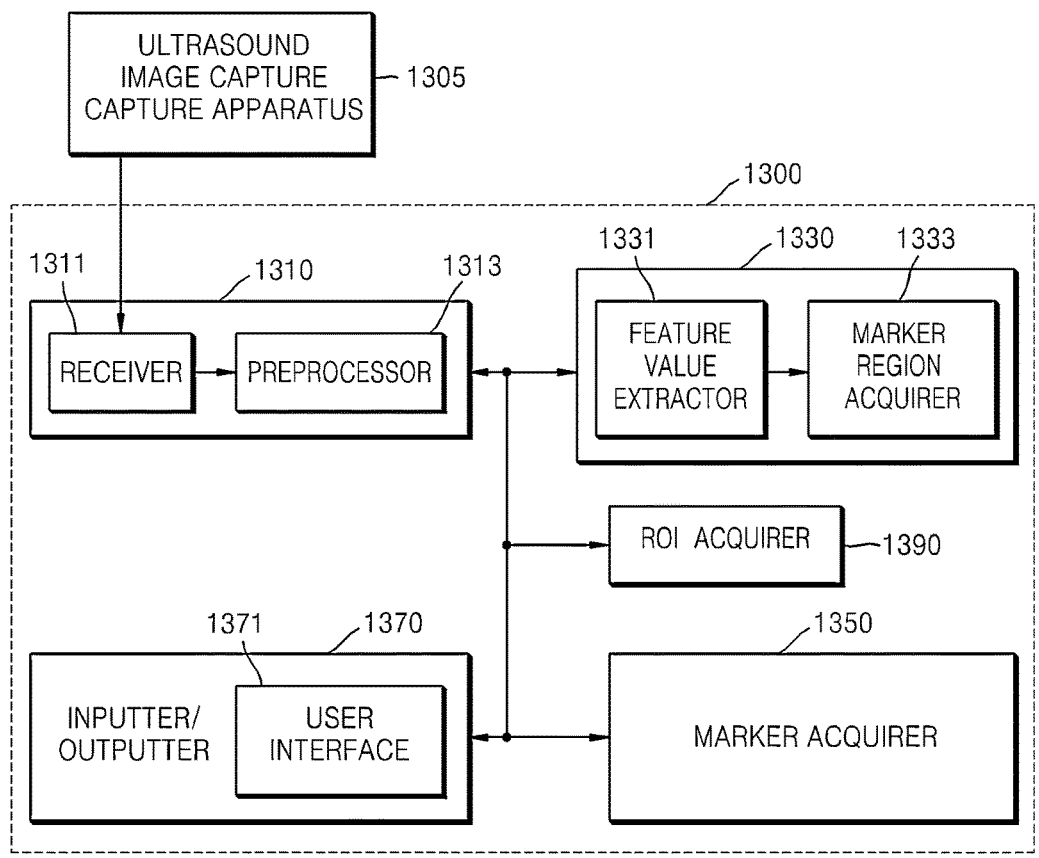
FIG. 13 is a block diagram of an image processing apparatus according to another exemplary embodiment.

FIG. 13 is a block diagram of an image processing apparatus 1300 according to another exemplary embodiment.

A region acquirer 1330 and a marker acquirer 1350, of the image processing apparatus 1300, correspond to the region acquirer 1230 and the marker acquirer 1250, described with reference to FIG. 12, respectively. Accordingly, descriptions overlapping with those of FIG. 12 are not repeated. Operations of the image processing apparatus 1300 illustrated in FIG. 13 are partially the same as operations of the image processing method 300 or image processing method 400, described with reference to FIGS. 1 through 11. Accordingly, descriptions overlapping with those of FIGS. 1 through 11 are not repeated.

Referring to FIG. 13, the image processing apparatus 1300 may be externally connected to an ultrasound image capture apparatus 1305. The ultrasound image capture apparatus 1305 generates an ultrasound image by applying an ultrasound signal to a predetermined portion of a human body. The ultrasound image capture apparatus can be, for example, any ultrasound machine or device which can create an ultrasound image.

The image processing apparatus 1300 may further include at least one of an image acquirer 1310, an inputter/outputter 1370, and an ROI acquirer 1390, compared to the image processing apparatus 1200.

The image acquirer 1310 acquires a heart ultrasound image. In detail, the image acquirer 1310 may acquire a heart ultrasound image captured by using an ultrasound Doppler signal. In addition, the image acquirer 1310 may acquire a processed heart ultrasound image by performing at least one of cropping, shifting, and noise reduction on the heart ultrasound image. The image acquirer 1310 may include a receiver 1311 and a preprocessor 1313.

The receiver 1311 receives the heart ultrasound image captured by the ultrasound image capture apparatus 1305. The receiver 1311 may perform operation 401 of the image processing method 400.

The preprocessor 1313 acquires an image-processed heart ultrasound image by performing an image processing on the heart ultrasound image transmitted from the receiver 1311. That is, the preprocessor 1313 may perform operation 405 of the image processing method 400.

The ROI acquirer 1390 acquires an ROI for measuring an MPI. The ROI acquirer 1390 may acquire an ROI including at least one myocardial performance period in a heart spectrum image. In detail, the ROI acquirer 1390 may perform operation 410 of the image processing method 400.

The region acquirer 1330 may include a feature value extractor 1331 and a marker region acquirer 1333.

The feature value extractor 1331 acquires at least one of a peak value corresponding to an input signal and a peak value corresponding to an output signal as a feature value. In detail, the feature value extractor 1331 may perform operation 415 of the image processing method 400.

A marker region acquirer 1333 acquires a plurality of marker areas based on feature values acquired by the feature value extractor 1331. In detail, the marker region acquirer 1333 may perform operation 420 of the image processing method 400.

The marker acquirer 1350 acquires markers for each of the acquired plurality of marker areas. In detail, the marker acquirer 1350 may perform operation 430 of the image processing method 400.

The inputter/outputter 1370 displays the heart spectrum image or receives a predetermined command or request from a user. The inputter/outputter 1370 may further include a user interface 1371. The inputter/outputter 1370 may display the marker areas and/or the heart spectrum image on which the markers are indicated.

The user interface 1371 functions as a user interface. A predetermined point of the heart spectrum image may be selected through the user interface 1371.

For example, when a predetermined point of the heart spectrum image is selected through the user interface 1371, at least one myocardial performance period of the heart spectrum image, which corresponds to the predetermined point, may be acquired as the ROI.

By using an image processing method and image processing apparatus according to one of the above-described exemplary embodiments, an MPI may be automatically measured. In detail, a marker may be accurately acquired from a limited marker area. In addition, the error rate due to a medical practitioner's skill, which occurs when manually measuring the MPI, may be decreased, and thus, the accuracy of acquiring the marker and MPI may be increased.

An image processing method according to one of the above-described exemplary embodiments can be embodied as computer readable codes or programs on a non-transitory computer readable recording medium. The non-transitory computer readable recording medium is any data storage device that can store data which can be thereafter read by a computer system. Examples of the non-transitory computer readable recording medium include read-only memory (ROM), random-access memory (RAM), CD-ROMs, magnetic tape, hard disks, floppy disks, flash memories, optical data storage devices, etc. The non-transitory computer readable recording medium can also be distributed over network coupled computer systems so that the computer readable code is stored and executed in a distributed fashion.

While exemplary embodiments have been particularly shown and described, it will be understood by those of ordinary skill in the art that various changes in form and details may be made therein without departing from the spirit and scope of the disclosure as defined by the following claims.

What is claimed is:

1. An image processing method, comprising:
acquiring, by an ultrasound image capture apparatus, a heart spectrum image;
obtaining, by an image processing apparatus, a region of interest (ROI) for measuring a myocardial performance index (MPI), based on signal levels of an input signal and an output signal of the heart spectrum image;
obtaining, by the image processing apparatus, a first peak value corresponding to the input signal at a first time point, a second peak value corresponding to the output signal at a second time point, and a third peak value corresponding to the input signal at a third time point;
obtaining, by the image processing apparatus, within the obtained ROI, a first marker area from the first time point to the second time point, and a second marker area from the second time point to the third time point;
obtaining, by the image processing apparatus, within a summation signal of the input signal and the output signal, a first lower peak value within the first marker area at a fourth time point, and a second lower peak value within the second marker area at a fifth time point;
obtaining, by the image processing apparatus, within the obtained ROI, a first detailed marker area from the first time point to the fourth time point, a second detailed marker area from the fourth time point to the second time point, a third detailed marker area from the second time point to the fifth time point, and a fourth detailed marker area from the fifth time point to the third time point; and
detecting, by the image processing apparatus without a user input, a respective marker in each of the first detailed marker area, the second detailed marker area, the third detailed marker area, and the fourth detailed marker area, wherein the respective marker is for measuring the MPI.

2. The image processing method of claim 1, wherein the obtaining of the ROI comprises:
receiving a selection of a predetermined point in the heart spectrum image, through a user interface screen; and
obtaining a myocardial performance period corresponding to the predetermined point, as the ROI, and
wherein the obtained myocardial performance period comprises one cycle of the input signal and one cycle of the output signal corresponding to the one cycle of the input signal.

3. The image processing method of claim 1, wherein the obtaining of the ROI comprises obtaining an interval comprising a plurality of myocardial performance periods, as the ROI, and
wherein each of the plurality of myocardial performance periods comprise one cycle of the input signal and one cycle of the output signal corresponding to the one cycle of the input signal.

4. The image processing method of claim 1, wherein the obtaining the ROI comprises:
sampling one myocardial performance period that includes one cycle of the input signal and one cycle of the output signal; and
using the sampled myocardial performance period, as the ROI.

5. The image processing method of claim 1, wherein the obtaining the first peak value, the second peak value and the third peak value comprises:
binarizing and cumulating each of the input signal and the output signal of the heart spectrum image; and
obtaining the first peak value corresponding to the binzarized and cumulated input signal at the first time point, the second peak value corresponding to the binzarized and cumulated output signal at the second time point, and the third peak value corresponding to the binzarized and cumulated input signal at the third time point.

6. The image processing method of claim 1, wherein the obtaining the first peak value, the second peak value and the third peak value comprises:
high-frequency filtering the heart spectrum image; and
obtaining the first peak value corresponding to the input signal at the first time point, the second peak value corresponding to the output signal at the second time point, and the third peak value corresponding to the input signal at the third time point, wherein the input signal and the output signal are of the high-frequency filtered heart spectrum image.

7. The image processing method of claim 1, wherein the detecting the respective marker comprises:
detecting a first marker at a sixth time point at which a first click signal of the input signal and the output signal is detected in the first marker area;
detecting a second marker at a seventh time point at which a first maximum gradient of the input signal and the output signal is detected in the second marker area;
detecting a third marker at an eighth time point at which a second click signal of the input signal and the output signal is detected in the third marker area; and
detecting a fourth marker at a ninth time point at which a second maximum gradient of the input signal and the output signal is detected in the fourth marker area.

8. The image processing method of claim 1, further comprising overlaying and displaying, on the heart spectrum image, the detected respective marker in each of the first detailed marker area, the second detailed marker area, the third detailed marker area, and the fourth detailed marker area.

9. The image processing method of claim 1, wherein the obtaining the ROI comprises obtaining the ROI, based on a first maximum signal level of the input signal and a second maximum signal level of the output signal.

10. The image processing method of claim 1, further comprising:
obtaining a heart ultrasound image that is captured by an ultrasound Doppler signal; and
obtaining a processed heart ultrasound image by performing at least one from among cropping, shifting, and noise reduction on the obtained heart ultrasound image.

11. The image processing method of claim 1, further comprising outputting a user interface screen for requesting an automatic setting or a manual setting of the ROI.

12. The image processing method of claim 11, further comprising receiving a selection of a predetermined period of the heart spectrum image or a predetermined point corresponding to the predetermined period, and obtaining the predetermined period as the ROI, based on the manual setting being requested through the user interface screen.

13. The image processing method of claim 11, further comprising obtaining, as the ROI, an interval that includes at least one myocardial performance period comprising one cycle of the input signal and one cycle of the output signal corresponding to the one cycle of the input signal, based on the automatic setting being requested through the user interface screen.

14. The image processing method according to claim 1, wherein the respective marker in each of the first detailed marker area, the second detailed marker area, the third detailed marker area, and the fourth detailed marker area indicates a respective time point in the heart spectrum image for calculating the MPI.

15. The image processing method according to claim 1, wherein the heart spectrum image comprises the input signal and the output signal of an ultrasound signal.

16. An image processing apparatus, comprising:
a memory storing instructions; and
a processor configured to execute the instructions to:
obtain a region of interest (ROI) to measure a myocardial performance index (MPI), based on signal levels of an input signal and an output signal of a heart spectrum image;
obtain a first peak value corresponding to the input signal at a first time point, a second peak value corresponding to the output signal at a second time point, and a third peak value corresponding to the input signal at a third time point;
obtain, within the obtained ROI, a first marker area from the first time point to the second time point, and a second marker area from the second time point to the third time point;
obtain, within a summation signal of the input signal and the output signal, a first lower peak value within the first marker area at a fourth time point, and a second lower peak value within the second marker area at a fifth time point;
obtain, within the obtained ROI, a first detailed marker area from the first time point to the fourth time point, a second detailed marker area from the fourth time point to the second time point, a third detailed marker area from the second time point to the fifth time point, and a fourth detailed marker area from the fifth time point to the third time point; and
detect, without a user input, a respective marker in each of the first detailed marker area, the second detailed marker area, the third detailed marker area, and the fourth detailed marker area, wherein the respective marker is for measuring the MPI.

17. The image processing apparatus of claim 16, wherein the processor is further configured to execute the instructions to:
receive a selection of a predetermined point in the heart spectrum image, though a user interface screen; and
obtain, as the ROI, a myocardial performance period corresponding to the predetermined point, and
wherein the myocardial performance period comprises one cycle of the input signal of the heart spectrum image and one cycle of the output signal corresponding to the one cycle of the input signal.

18. The image processing apparatus of claim 16, wherein the processor is further configured to execute the instructions to obtain, as the ROI, an interval comprising a plurality of myocardial performance periods, and
wherein each of the plurality of myocardial performance periods comprises one cycle of the input signal and one cycle of the output signal of the heart spectrum image corresponding to the one cycle of the input signal.

19. The image processing apparatus of claim 16, wherein the processor is further configured to execute the instructions to:
sample one myocardial performance period that includes one cycle of the input signal and one cycle of the output signal; and
use the sampled myocardial performance period, as the ROI.

20. The image processing apparatus of claim 16, wherein the processor is further configured to execute the instructions to:
binarize and cumulate each of the input signal and the output signal of the heart spectrum image; and
obtain the first peak value corresponding to the binzarized and cumulated input signal at the first time point, the second peak value corresponding to the binzarized and cumulated output signal at the second time point, and the third peak value corresponding to the binzarized and cumulated input signal at the third time point.

21. The image processing apparatus of claim 16, wherein the processor is further configured to execute the instructions to:
high-frequency filter the heart spectrum image; and
obtain the first peak value corresponding to the input signal at the first time point, the second peak value corresponding to the output signal at the second time point, and the third peak value corresponding to the input signal at the third time point, wherein the input signal and the output signal are of the high-frequency filtered heart spectrum image.

22. The image processing apparatus of claim 16, wherein the processor is further configured to execute the instructions to:
detect a first marker at a sixth time point at which a first click signal of the input signal and the output signal is detected in the first marker area;
detect a second marker at a seventh time point at which a first maximum gradient of the input signal and the output signal is detected in the second marker area;
detect a third marker at an eighth time point at which a second click signal of the input signal and the output signal is detected in the third marker area; and
detect a fourth marker at a ninth time point at which a second maximum gradient of the input signal and the output signal is detected in the fourth marker area.

23. The image processing apparatus of claim 16, wherein the processor is further configured to execute the instructions to overlay and control to display, on the heart spectrum image, the detected respective marker in each of the first detailed marker area, the second detailed marker area, the third detailed marker area, and the fourth detailed marker area.

24. The image processing apparatus of claim 16, further comprising an image acquirer configured to:
   obtain a heart ultrasound image that is captured by using an ultrasound Doppler signal; and
   obtain a processed heart ultrasound image by performing at least one from among cropping, shifting, and noise reduction on the obtained heart ultrasound image.

25. The image processing apparatus of claim 16, further comprising a user interface configured to output a user interface screen for requesting an automatic setting or a manual setting of the ROI.

26. The image processing apparatus of claim 25, wherein the user interface is further configured to, based on the manual setting being requested through the user interface screen, receive a selection of a predetermined period of the heart spectrum image or a predetermined point corresponding to the predetermined period, and obtain the predetermined period as the ROI.

27. The image processing apparatus of claim 25, wherein the user interface is further configured to, based on the automatic setting being requested through the user interface screen, obtain, as the ROI, an interval that includes at least one myocardial performance period comprising one cycle of the input signal and one cycle of the output signal corresponding to the one cycle of the input signal.

28. An ultrasound imaging device, comprising:
   a receiver configured to obtain a spectral image of a heart; and
   a processor configured to:
      obtain a region of interest (ROI) for measuring a myocardial performance index (MPI), based on signal levels of an input signal and an output signal of the spectral image of the heart;
      obtain a first peak value corresponding to the input signal at a first time point, a second peak value corresponding to the output signal at a second time point, and a third peak value corresponding to the input signal at a third time point;
      obtain, within the obtained ROI, a first marker area from the first time point to the second time point, and a second marker area from the second time point to the third time point;
      obtain, within a summation signal of the input signal and the output signal, a first lower peak value within the first marker area at a fourth time point, and a second lower peak value within the second marker area at a fifth time point; and
      obtain, within the obtained ROI, a first detailed marker area from the first time point to the fourth time point, a second detailed marker area from the fourth time point to the second time point, a third detailed marker area from the second time point to the fifth time point, and a fourth detailed marker area from the fifth time point to the third time point; and
   detect, without a user input, a respective marker in each of the first detailed marker area, the second detailed marker area, the third detailed marker area, and the fourth detailed marker area, wherein the marker is for measuring the MPI.

* * * * *